United States Patent
Wang

(10) Patent No.: US 9,498,184 B2
(45) Date of Patent: Nov. 22, 2016

(54) BREAST ULTRASOUND SCANNING DEVICE

(71) Applicant: Shih-Ping Wang, Los Altos, CA (US)

(72) Inventor: Shih-Ping Wang, Los Altos, CA (US)

(73) Assignee: QVIEW MEDICAL, INC., Los Altos, CA (US)

( * ) Notice: Subject to any disclaimer, the term of this patent is extended or adjusted under 35 U.S.C. 154(b) by 12 days.

(21) Appl. No.: 14/076,989

(22) Filed: Nov. 11, 2013

(65) Prior Publication Data

US 2014/0066769 A1    Mar. 6, 2014

Related U.S. Application Data

(63) Continuation-in-part of application No. 13/296,023, filed on Nov. 14, 2011, now Pat. No. 8,579,819, which is a continuation of application No. 11/513,481, filed on Aug. 30, 2006, now abandoned.

(60) Provisional application No. 61/769,913, filed on Feb. 27, 2013, provisional application No. 60/713,282, filed on Sep. 1, 2005.

(51) Int. Cl.
  *A61B 8/14*   (2006.01)
  *A61B 8/08*   (2006.01)
  *A61B 8/00*   (2006.01)

(52) U.S. Cl.
  CPC ............... *A61B 8/14* (2013.01); *A61B 8/0825* (2013.01); *A61B 8/4209* (2013.01); *A61B 8/4218* (2013.01); *A61B 8/4455* (2013.01); *A61B 8/4461* (2013.01); *A61B 8/4494* (2013.01); *A61B 8/463* (2013.01); *A61B 8/145* (2013.01);

(Continued)

(58) Field of Classification Search
  CPC ..... A61B 8/08; A61B 8/4416; A61B 8/5238
  USPC ................... 600/437, 440, 445, 459
  See application file for complete search history.

(56) References Cited

U.S. PATENT DOCUMENTS

| 4,338,948 A | 7/1982 | Perez-Mendez et al. |
| 4,841,977 A * | 6/1989 | Griffith et al. ............... 600/439 |

(Continued)

FOREIGN PATENT DOCUMENTS

| JP | 2003088525 | 3/2003 |
| JP | 2003088525 A * | 3/2003 |

(Continued)

OTHER PUBLICATIONS

T.A. Stavros, "Breast Ultrasound," 2003, Philadelphia: Lippincott Williams & Wilkins, pp. 43, 57, and 59.*

(Continued)

*Primary Examiner* — Tse Chen
*Assistant Examiner* — Nate S Sunwoo
(74) *Attorney, Agent, or Firm* — Cooper & Dunham LLP

(57) ABSTRACT

An apparatus and a method are disclosed for obtaining ultrasound images of a patient's breast that is chestwardly compressed with a template that is essentially planar and rotates relative to the breast while one or more ultrasound transducers moving with the template take 2D images of the breast through one or more respective radially oriented slots in the template, preferably through a membrane that is porous to a gel. The 2D images are processed into slice images representing breast slices of desired thicknesses and orientation that are displayed alone or with some of the 2D images, preferably pairs of orthogonally disposed 2D images.

26 Claims, 11 Drawing Sheets

(52) U.S. Cl.
CPC ............ *A61B 8/4281* (2013.01); *A61B 8/4405* (2013.01); *A61B 8/483* (2013.01); *A61B 8/54* (2013.01)

(56) References Cited

U.S. PATENT DOCUMENTS

| | | | |
|---|---|---|---|
| 4,886,494 A | 12/1989 | Morifugi | |
| 5,938,612 A * | 8/1999 | Kline-Schoder et al. | 600/459 |
| 6,146,377 A * | 11/2000 | Lee et al. | 606/13 |
| 6,475,150 B2 | 11/2002 | Haddad | |
| 6,504,157 B2 | 1/2003 | Juhi | |
| 7,597,663 B2 * | 10/2009 | Wang et al. | 600/437 |
| 7,828,733 B2 | 11/2010 | Zhang et al. | |
| 7,940,966 B2 | 5/2011 | Yu | |
| 2003/0167004 A1 * | 9/2003 | Dines et al. | 600/437 |
| 2004/0015080 A1 * | 1/2004 | Kelly et al. | 600/437 |

FOREIGN PATENT DOCUMENTS

| | | |
|---|---|---|
| WO | WO 02/30287 | 4/2002 |
| WO | WO 03/103500 A1 | 12/2003 |
| WO | WO 03103500 A1 * | 12/2003 |
| WO | WO 2004/305232 A2 | 4/2004 |
| WO | WO 2005/104729 A2 | 10/2005 |
| WO | WO 2007/014292 | 2/2007 |

OTHER PUBLICATIONS

D'Astous et al, "Original contribution: Frequency dependence of ultrasound attenuation and backscatter in breast tissue," 1986, Ultrasound in Med. & Biol. vol. 12, pp. 795-808.*

"*Breast Ultrasound*" by A. Thomas Stavros (Publisher: Lipponcott Williams & Wilkins 2004).

"*The Practice of Breast Ultrasound: Techniques, Findings, Differential Diagnosis*" by Helmut Madjar and Ellen Mendelson (Publisher: Thieme 2008).

"Guidelines from IBUS (International Breast Ultrasound School) for Ultrasonic Examination of the Breast" (Edited by Helmut Madjar et al; Published in *European Journal of Ultrasound* 1999; vol. 9, pp. 99-102).

F.T. D'Astous and Foster Frequency Dependence of Ultrasound Attenuation and Backscatter in Breast Tissue(published in *Ultrasound in Med. & Biol.* 1986; vol. 12, pp. 795-808).

"*Rapid image stitching and computer-aided detection for multipass automated breast ultrasound*" reported by RF Change et al. (published in Medical Physics 2010; vol. 37, pp. 2063-2073).

T.A. Stavos, Breast Ultrasound, 2003, Philadelphia: Lippincott Williams, pp. 57 and 59.

* cited by examiner

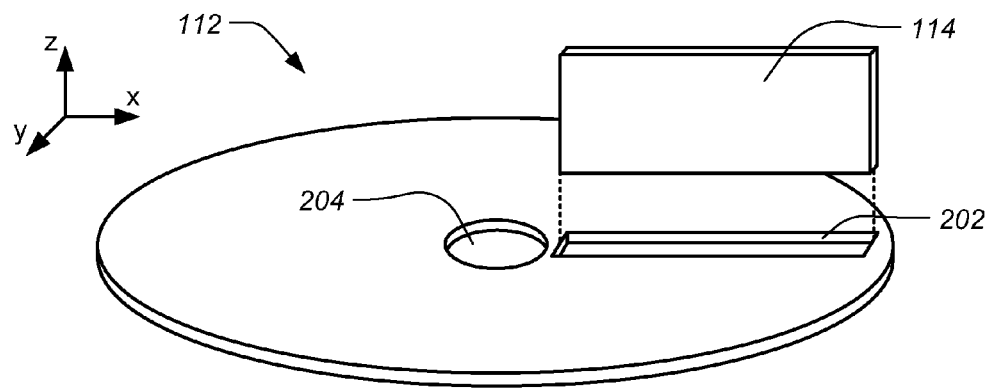
*FIG. 2*
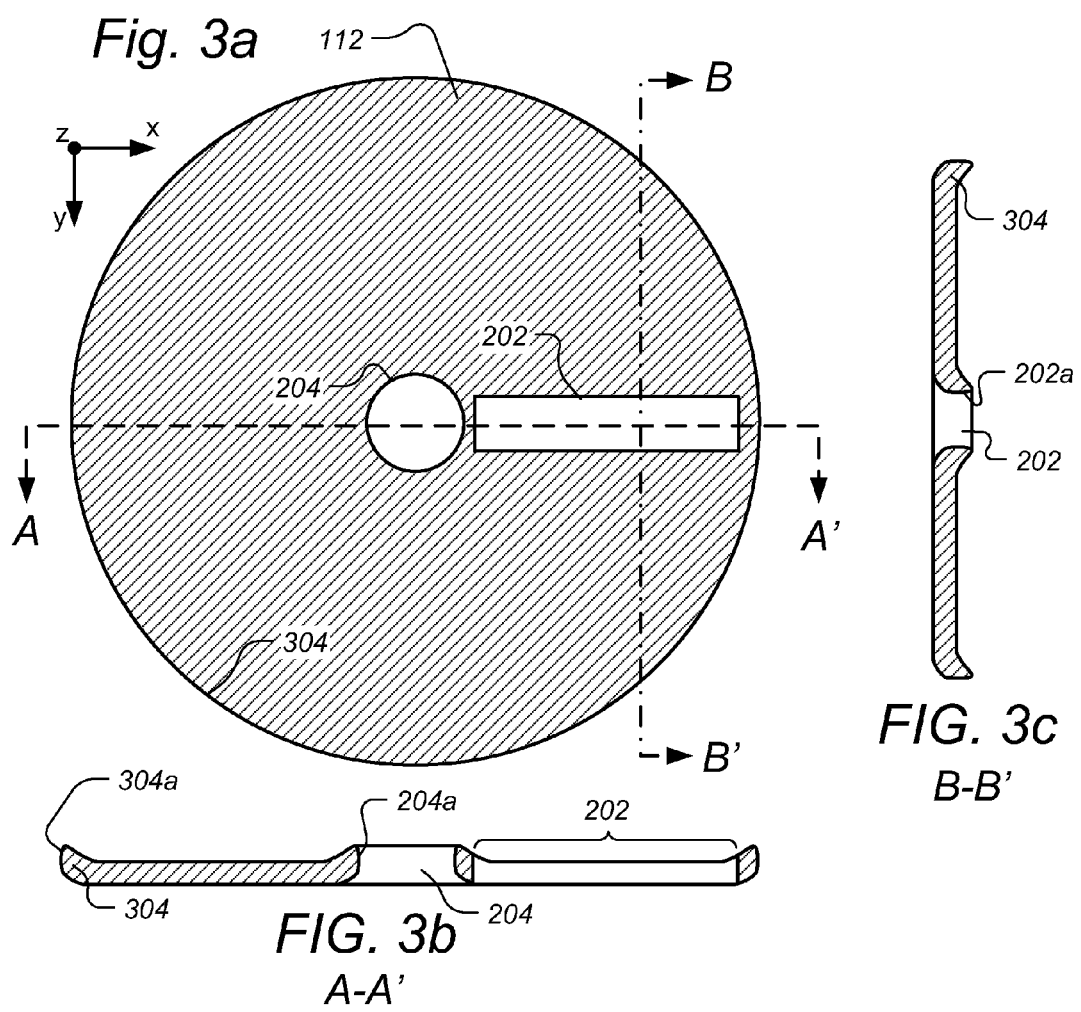
*Fig. 3a*
*FIG. 3c*
B-B'
*FIG. 3b*
A-A'

FIG. 12a
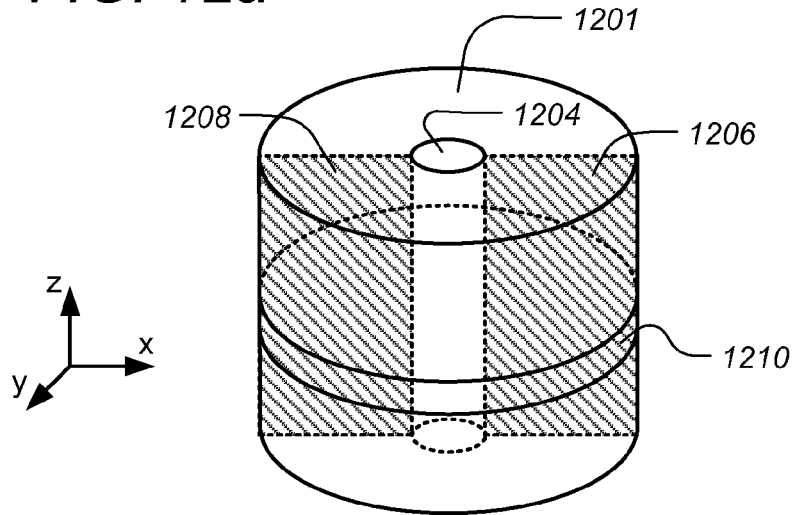
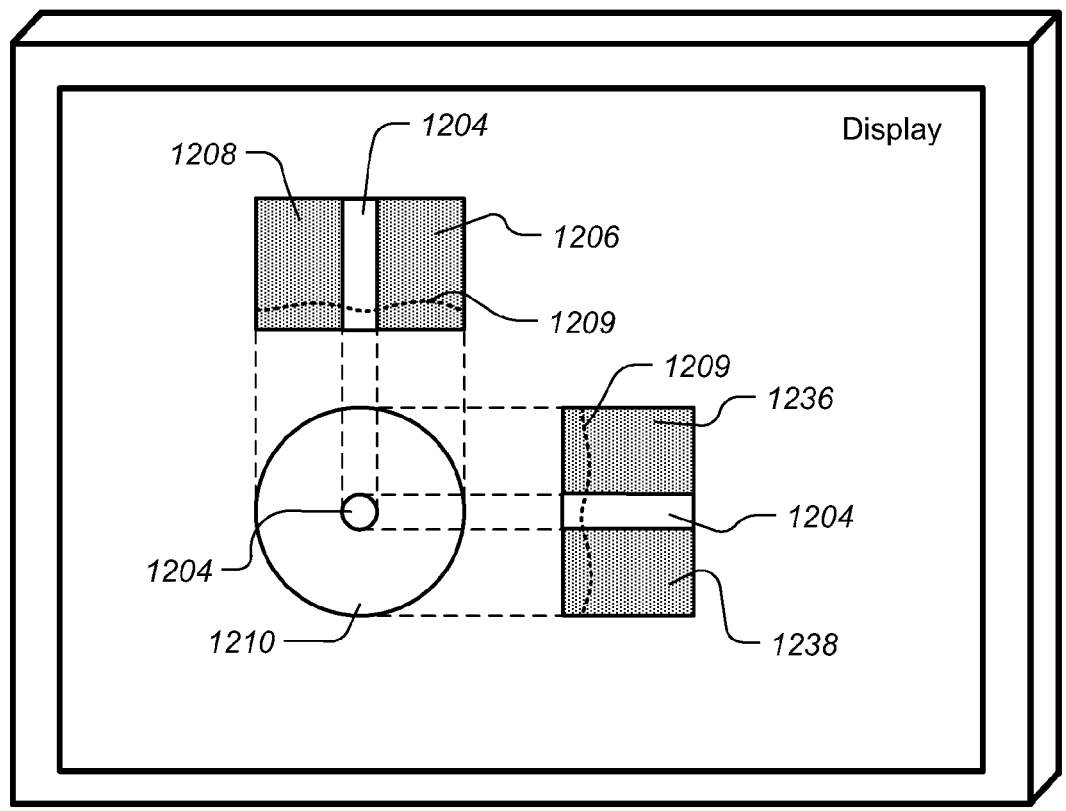
FIG. 12b

BREAST ULTRASOUND SCANNING DEVICE

CROSS-REFERENCE TO RELATED APPLICATIONS

This application claims the benefit of U.S. Provisional Application 61/769,913 filed Feb. 27, 2013. This application is a continuation-in-part of U.S. application Ser. No. 13/296,023 filed Nov. 14, 2011 (which was published as US 2012/0089026 A1 and is scheduled to issue as U.S. Pat. No. 8,579,819 on Nov. 12, 2013), which is a continuation of U.S. application Ser. No. 11/513,481 filed Aug. 30, 2006 and claiming the benefit of U.S. Provisional Application No. 60/713,282 filed on Sep. 1, 2005. The entire content of all of the above applications is hereby incorporated by reference herein. Also incorporated by reference herein are the contents of all of the patent applications and patents and other publications cited below.

FIELD

This patent specification relates to medical imaging. More particularly, this patent specification relates to breast ultrasound imaging using chestward compression of a breast and automated scanning with a transducer secured to a radial scanning template.

BACKGROUND

Volumetric breast ultrasound scanning usually involves a rectilinear movement of a linear-array ultrasound transducer relative to the breast tissue of a patient, with successive scanning lines parallel to one another, and processing of resultant ultrasound echoes to form a data volume representing local (e.g., voxel) values of at least one acoustic property of the scanned breast. Volumetric ultrasound scanning of the breast has been proposed as a complementary modality for breast cancer screening. One example is discussed in U.S. Pat. No. 7,828,733 and involves using a full-field breast ultrasound (hereinafter "FFBU") scanning apparatus that chestwardly compresses a breast, and a rectilinear transducer translation mechanism that maintains an ultrasound transducer in contact with the breast, as discussed, for example, in WO 2007/014292, which employs scanning through a fabric material porous to an ultrasound coupling agent and has the advantage of reducing image artifacts such as those believed to be due to air bubbles.

One of the most important factors in breast ultrasound is image quality, which is generally defined by parameters such as image spatial resolution, signal dynamic range, and relative tissue image contrast. Image quality is very dependent on the frequency of the ultrasound. Major text books on breast ultrasound, such as "Breast Ultrasound" by A. Thomas Stavros (Publisher: Lipponcott Williams & Wilkins 2004) (hereinafter 'Stavros 2004') and "The Practice of Breast Ultrasound: Techniques, Findings, Differential Diagnosis" by Helmut Madjar and Ellen Mendelson (Publisher: Thieme 2008), counsel against using ultrasound frequencies below 7 to 7.5 MHz when seeking to achieve acceptable breast images. These books explain that much higher ultrasound frequencies, if possible as high as 12 MHz, should be used for breast imaging. "Guidelines from IBUS (International Breast Ultrasound School) for Ultrasonic Examination of the Breast" (Edited by Helmut Madjar et al; Published in European Journal of Ultrasound 1999; Vol. 9, pages 99-102) also recommends not using ultrasound frequencies below 7.5 MHz for breast imaging. However, breast ultrasound imaging at higher frequencies presents challenges because the ultrasound attenuation of breast tissue increases rapidly with ultrasound frequency, as shown by D'Astous and Foster (published in Ultrasound in Med. & Biol. 1986; Vol. 12, pages 795-808) (hereinafter "D'Astous and Foster"). With an attenuation coefficient of 1 to 2 dB/cm-MHz respectively for breast cancer and parenchyma tissues, at an ultrasound frequency of 7 MHz the resulting attenuation would reach the undesirable range of 42 to 84 dB for a 6 cm thickness of breast tissue. FIGS. 2-37 on page 34 of Stavros 2004 shows a penetration depth of around 3.5 cm for a breast ultrasound image obtained at 12 MHz. Current commercially available FFBUs are believed to operate in the range of ultrasound frequencies from 8 MHz to 14 MHz in order to obtain acceptable image quality for the range of breast sizes.

The known current commercially available FFBU scanning devices are rectilinear scanners, with scanning lines essentially parallel to each other as explained above. A significant challenge in these scanners is trying to fit a rectangular scan area over a round breast. Frequently each breast has to be scanned two to five or more times in overlapping set of scans. Even with good image stitching techniques, such as "Rapid image stitching and computer-aided detection for multipass automated breast ultrasound" reported by RF Change et al. (published in Medical Physics 2010; Vol. 37, pages 2063-2073), it is difficult to accurately stitch several separate scans of a breast into one single set forming a single image. Thus, a current practice of reading images of commercial FFBU is to view each of the several scans separately and independently as each scan covers different, although partially overlapping, parts of the breast. As a result, such multiple scans for each breast would require in longer interpretation times by physicians. Another problem for such multiple scans is an increase in the time for each patient in the scan examination room, which has a direct negative impact on: (1) patient throughput; and (2) revenue generation per FFBU per year.

There is a proposal for non-rectilinear FFBU scanning in WO 03/103500, which is not believed to have been commercially implemented. The reference proposes the use of a cone-shaped tissue molding element having a hole through which an ultrasonic transducer scans the breast as the molding element rotates relative to the breast. The figure in the reference appears to show that the wall of the molding element converges at an angle of about 90°. In comparison to one or more of the preferred embodiments described herein, where the scanned breast is flattened against the patient's chest wall, using such a 90° molding element would mean scanning through a much greater thickness of breast tissue. This would bring about two major shortcomings: (1) poorer image quality; and (2) limited range in size of breasts that can be scanned. This is because lower ultrasound frequency would have to be used for the greater thickness of scanned breast tissue, particularly in the case of larger breasts that would require ultrasound frequency below the minimum recommended 7.5 MHz. Early FFBU developments involving laterally compressed breasts (as in mammography), such as discussed in Pat. Publ. US 2006/0173303 A1, produced images of lower quality than current devices that scan a chestwardly compressed breast because lower ultrasound frequencies had to be used for larger breasts in such early development FFBU devices, and resulted in a change-over to chestward compression. Additional issues arise in the rectilinear scanning devices referred to above and in the devices discussed in WO 03/103500, as would be readily apparent to one skilled in the art in view of the disclosure in this patent specification.

SUMMARY

An apparatus and related methods for ultrasonically scanning a breast and displaying the volumetric information are provided, the apparatus comprising an ultrasound transducer and a radial scanning template that compresses the breast in a generally chestward direction, the radial scanning template preferably being round and preferably having an opening in the center of the template through which the breast's nipple can protrude. The radial scanning template has a slot-shaped opening extending generally radially outwardly from the center, through which opening the ultrasound transducer scans the breast as the template rotates over the breast. In one embodiment, the scanning template is "essentially planar," which in this patent specification designates a template that may depart from absolute planarity only such that a difference between the levels of the central opening and the periphery of the template is less than that for a template shaped as a truncated cone that has a similar central opening and a sidewall that converges at an angle in the range of more than 175° to about 180°, in which case it can be said that the template deviates from absolute planarity by an angle that is in a range of less than 2.5° to 0° and is called a departure angle in this patent specification. In other embodiments the departure angle can be in the range of 5° to 0°, 10° to 0°, 15° to 0°, or 20° to 0°, depending on the length and shape of the transducer used. The template, if not absolutely planar, can be shaped substantially as a shallow truncated cone or it can be shaped like a shallow inverted bowl, and preferably has a generally central opening. The template's concave side is configured to face and flatten a patient's breast chestwardly. The template preferably has a round circumference and may but need not be circular. The inner (breast-facing) wall may curve in one or two dimensions. The template can be cam-shaped in outline, or close to oval or even close to square or rectangular so long as it has a sufficiently rounded corners to allow for rotation over a chestwardly compressed breast as in the examples described below. The breast-facing side of the elongated ultrasound transducer that is used with the template can extend along a straight line or along a curved line so that a concave surface would contact the breast, to better match the somewhat rounded, convex side of a breast flattened with the template. The edges of the breast-facing side of the transducer and of the template and its openings preferably are sufficiently rounded or beveled to avoid uncomfortable contact of sharp edges or corners with the breast.

There are significant advantages in employing an essentially planar scanning template that can effectively flatten breast tissue against the chest wall and thereby reduce the required scan depth and make consistently possible and practical the use of higher ultrasound frequencies. The higher ultrasound frequencies (e.g., 8 MHz-15 MHz) then can penetrate to the required depth and result in superior image quality over images from lower ultrasound frequencies (e.g. below 7.5 MHz, which would be necessary for scans of thicker breast tissues in a manner proposed in WO 03/103500). An essentially planar radial scan configuration also allows easier volumetric information reconstruction as well as display, which in turn provides ease in the interpretation of displayed images by radiologists. Such scanning templates are particularly effective for ultrasonically scanning the breast of a supine patient, although application to other patient positions (e.g., prone, upright, decubitus) is within the scope of the preferred embodiments.

In one preferred embodiment, a hole in the center of the radial template allows the nipple to protrude through the template during the scan. This overcomes image distortion and artifact problems of FFBU scanning devices such as those proposed in U.S. Pat. No. 7,828,733 and in WO 02/30287, which scan over the nipple during the scanning process and push the nipple into the breast. WO 02/30287 recognizes the problem but proposes a different solution, namely, using a nipple pad in an effort to reduce the image distortion and artifact problem caused by scanning over the nipple. The hole in the center of the templates disclosed in this patent specification also serves as a natural locator for the nipple, in contrast with the case of known scanning devices where health professionals manually find the nipple in the image and mark its location in scanned images.

This radial scan configurations disclosed in this patent specification are capable of covering a breast with a single scan by using a single transducer, whereas a rectilinear scanning commercial FFBU, such as in U.S. Pat. No. 7,828,733, could cover a breast with 2 to 5 scans by using a longer and thus more expensive transducer. Rectilinear scanning such as in WO 02/30287 uses a greater number of scans to cover a breast, which makes reconstruction of 3D volumetric images more difficult due to breast motion caused by the scanning process and due to image stitching artifacts. Significant advantages of a single scan over multiple scans include: (1) reduced interpretation time; (2) increased patient throughput; and (3) increased revenue generation for FFBU owners. According to some embodiments, image quality of a single scan device is further improved by slowing down the scan speed, which is not easily accomplished by current FFBUs when performing multiple scans without further reducing patient throughput.

Preferably, the radial scanning templates disclosed in this patent specification comprise a material that is semi-rigid, or substantially rigid, that sufficiently flattens the breast chestwardly for scanning and is sufficiently optically translucent to facilitate visualizing the breast for positioning and scanning.

According to one preferred embodiment, the ultrasound transducer is in direct contact with the breast skin through a slot-shaped opening in the template. In another preferred embodiment, a fabric porous to an ultrasound coupling agent such as gel extends across the slot-shaped opening in the template, and the ultrasound transducer scans the breast through the porous fabric. In still another preferred embodiment, at least the inner side of the entire template is covered with a removable sock made of such a porous fabric. In yet another preferred embodiment, the patient wears a brassiere-shaped article where at least the portion covering the breasts is made of such a porous fabric and may have holes through which the nipples protrude, and the templates described in this patent specification are positioned over the fabric, with a nipple protruding through a central hole in the template.

According to one preferred embodiment, a scanning template has only one radially extending slot-shaped opening and only a single ultrasound transducer scans the breast. The radial scanning template rotates through 360 degrees plus an overlap angle, if desired, during the breast ultrasound scan, the overlap angle preferably being in a range of 5° to 45°. Thus, breast tissue within the overlap angle is scanned twice. The information from such dual scanning of some tissue can be used to reduce potential discontinuities in the resulting volumetric representation of the breast associated with the start-stop locations of the scan, using suitable blending of the duplicated scan information.

According to another preferred embodiment, different radial scanning templates and/or transducers, that have different sizes and shapes, are used to fit different sizes and shapes of the breasts to be scanned.

In still another preferred embodiment, a concavely curved transducer is used with a similarly concavely curved template.

According to another preferred embodiment, a plurality of ultrasound transducers and a corresponding plurality of slot-shaped openings in a template are provided. In general, where there are N transducers, a full volumetric scan can be achieved by rotating the radial scanning template by 360/N degrees, plus an overlap angle, if desired, that can be less than 5° in the case of a sufficient number of transducers scanning concurrently.

In one embodiment, at least two ultrasound transducers are used that have different lengths corresponding to different central hole-to-periphery distances around the radial scanning template. Each ultrasound transducer scans a different coronal sector of the breast. In one example, a longer ultrasound transducers scans the coronal sector of the breast that is near the axilla, which sector usually extends farther out from the nipple than other breast sectors, and a shorter ultrasound transducer scans other portions of the breast.

In one embodiment, the transducer is made of a single linear array of transducer elements (sometimes referred to as 1D array). In another preferred embodiment, the transducer is made of multiple arrays parallel to one another (sometimes referred to as 1.25D, 1.5D, 2D, etc. arrays). This type of multiple-arrayed transducers can provide better lateral spatial resolution than a single array transducer.

In one preferred embodiment, the nipple and sub-areola regions can be partially covered with beam-steering of the scanning ultrasound beam from the transducer. In another embodiment, the nipple and sub-areola regions can be separately scanned manually, for example with a handheld ultrasound transducer.

The scan with a essentially planar radial template as disclosed in this patent specification can generate a simpler set of images, which permits easier and more accurate reconstruction and display of 3D information including, for example, coronal slice images. This scan configuration also allows a cine review of original 2D images that facilitates image interpretation.

BRIEF DESCRIPTION OF THE DRAWING

FIG. 2 illustrates in a perspective exploded view an essentially planar scanning template and an ultrasound transducer for scanning a chestwardly flattened breast.

FIG. 3a is a top plan view of an essentially planar scanning template; FIG. 3b is a cross-section through lines A-A', and FIG. 3c is a cross-section through lines B-B'. FIGS. 3a and 3b are a plan view and a cross-sectional view, respectively, of an essentially planar scanning template

FIG. 4b is a top view of the template of FIG. 4a.

FIG. 12a illustrates a 3D scanned breast volume and its relationship with original 2D scanned slices.

FIG. 12b illustrates a display of a coronal slice and associated orthogonal views of original 2D scans.

DETAILED DESCRIPTION

Figure 1:
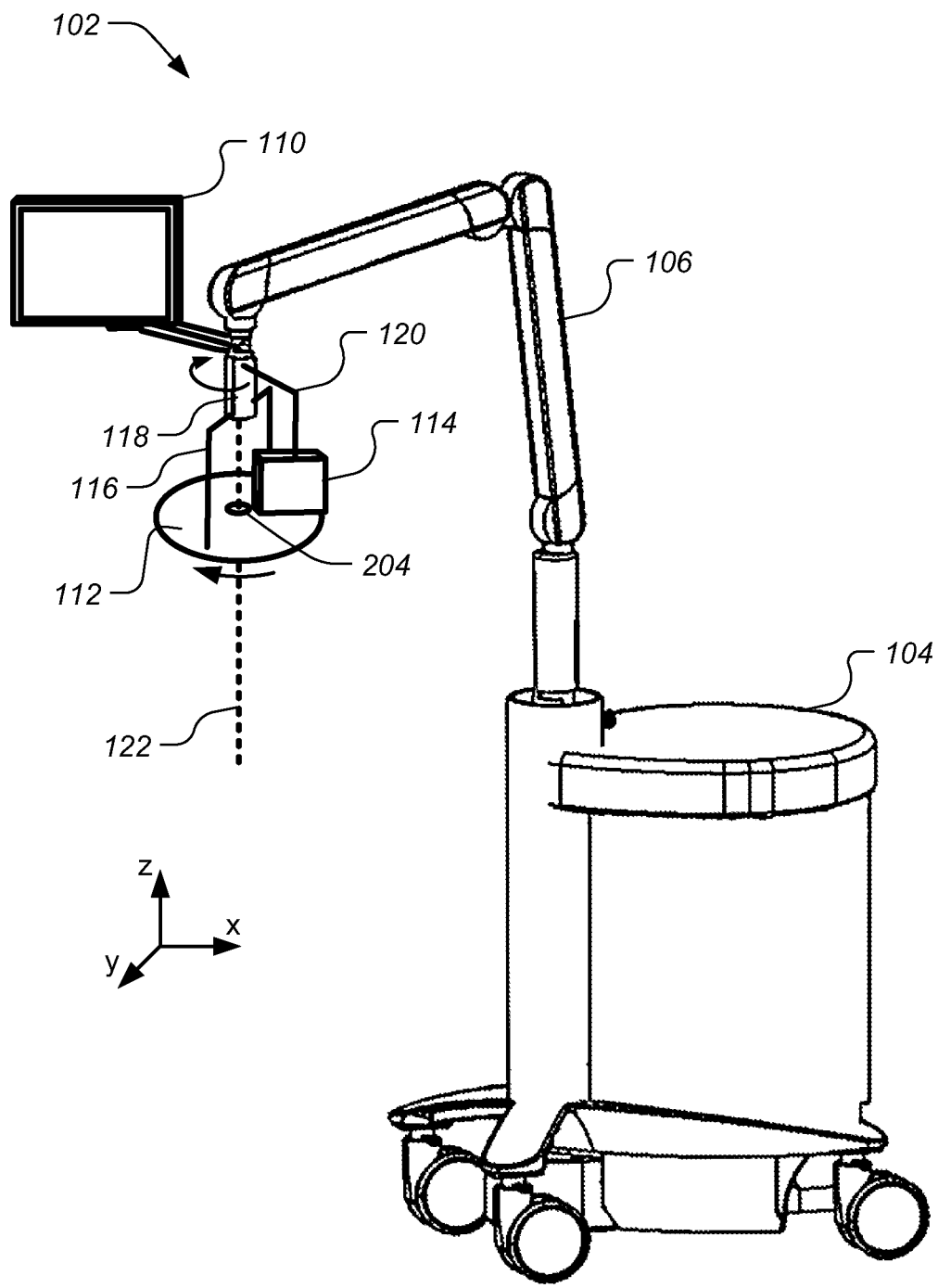
FIG. 1 illustrates in a perspective view a full-field breast ultrasound (FFBU) device.

FIG. 1 illustrates a perspective view of a full-field breast ultrasound (FFBU) scanning apparatus 102 according to a preferred embodiment, comprising a frame 104 that may contain an ultrasound processor, a movable support arm 106, and a monitor 110 connected to the support arm 106. FFBU scanning apparatus 102 further comprises an essentially planar radial scanning template 112 and an ultrasound transducer 114. The radial scanning template 112 is configured to chestwardly compress a breast of a patient (e.g., a supine patient) while rotating around an axis 122, preferably centered on the nipple hole 204. The ultrasound transducer 114 rotates with the radial scanning planar template 112 and scans the breast through a slot-shaped, radially extending opening therein. For reference purposes herein, the +z direction refers to an outward direction away from the patient's chest, the x-axis refers to a left-right direction relative to the supine patient, and the y-axis refers to a head-to-toe direction. The x-y plane thus corresponds to a coronal plane of a breast, the x-z plane corresponds to an axial plane, and the y-z plane corresponds to a sagittal plane.

Also illustrated in FIG. 1 is a rigid, two-pronged connector 116 and a rigid, single-arm connector 120 that mechanically connect the radial scanning template 112 and the ultrasound transducer 114, respectively, to an actuator assembly 118 for achieving the movement functionalities described herein. It should be understood that the mechanical elements 116-120 in FIG. 1 are drawn by way of a conceptual example only and not to scale. In view of the disclosure in this patent specification, a person skilled in the art would be readily able to construct the various mechanical/electrical linkages, actuators, motors, sensors, etc., required to achieve the described mechanical functionalities without undue experimentation. Accordingly, such mechanical/electrical details are mostly omitted from the drawings herein for clarity of description.

Preferably, support arm 106 is configured and adapted such that the overall compression/scanning assembly 112-120 (i) is neutrally buoyant in space, or (ii) has a light net downward weight (e.g., 2-3 pounds) for breast compression, while allowing for easy user manipulation. Optionally, the support arm 106, the template, and/or the transducer(s) can comprise potentiometers and/or other sensors (not shown) to allow force, position, and/or orientation sensing for the overall compression/scanning assembly 112-120, the template, and/or the transducer(s). Other types of force, position, and/or orientation sensing (e.g., gyroscopic, magnetic, optical, radio frequency (RF)) can be used instead or in addition.

Within frame 104 there can be provided a fully functional ultrasound engine for driving one or more ultrasound transducers and generating volumetric breast ultrasound data and images from the scans in conjunction with the associated position and orientation information. The volumetric scan data can be transferred to one or more other computer systems for further processing using any of a variety of data transfer methods known in the art. A general purpose computer, which can be implemented on the same computer as the ultrasound engine, can be provided for general user interfacing and system control. The general purpose computer can be a self-contained stand-alone unit, or can be remotely controlled, configured, and/or monitored by a remote station connected across a network.

FIGS. 2, 3a, 3b, and 3c illustrate more detailed views of an essentially planar radial scanning template 112 in accordance with a preferred embodiment. Radial scanning template 112 preferably is rounded, e.g., has a generally circular shape, and defines therein a slot-shaped opening 202 that extends generally radially from a central opening 204. The slot-shaped opening 202 is dimensioned to allow an ultrasound transducer 114 to at least partially pass therethrough to scan the breast. Although shown as a one-dimensional array in FIG. 2, the ultrasound transducer 114 more generally can be multiple-arrayed (sometimes referred to as 1.25D, 1.5D, 2D, etc.), or hybridization thereof without departing from the scope of the preferred embodiments. In one preferred embodiment, the FFBU scanning apparatus 102 is provided with an interchangeable (and/or disposable) set of essentially planar radial scanning templates 112 that are differently sized or shaped for differently-sized or shaped breasts. In one example, eight (8) different radial scanning templates having base diameters of 4 inches, 5 inches, 6 inches, 7 inches, 8 inches, 9 inches, 10 inches and 12 inches are provided. Exemplary diameters for the central opening 204 range between about 0.25" to 1" (0.25 inches to 1 inch). The slot-shaped opening 202 may have a width typically in the range of 0.25" to 1" depending on the size of the ultrasound transducer to be inserted therethrough. In addition, a selection of templates can be provided that are not essentially planar but have greater departure angles.

In one preferred embodiment, the ultrasound transducer 114 is supported and actuated independently of the radial scanning template 112. In another preferred embodiment, the ultrasound transducer 114 is integral with, clipped to, or otherwise secured to or fused with or mounted on the radial scanning template 112 for joint support and/or actuation.

With reference to FIG. 3a, the essentially planar radial scanning template 112 is shaped as a circular plate having a circular hole 204 located at the center of the circular plate 304 and a radially extending slot-shaped opening 202 from near the hole 204 to near the periphery of plate 304. FIG. 3b illustrates a sectional view along lines A-A', and FIG. 3c illustrates a sectional view along lines B-B.

In one preferred embodiment, the radial scanning template 112 is formed of a transparent or at least translucent material having mechanical properties similar to those of 40-mil thick polycarbonate plastic, 40-mil polystyrene plastic, or a mechanically equivalent thickness of polyethylene terephthalate (PETE) plastic. In this embodiment, there is some amount of "give" or flexibility to the template 102, providing some degree of comfort to the patient as well as adaptability to differently-sized breasts while at the same time providing for substantial stabilization of the breast tissue for reliable volumetric imaging of the breast. Such a template is called "semi-rigid" in this patent specification. In another preferred embodiment, the material for template 102 comprises a transparent or at least translucent material such as 140-mil thick glass, 140-mil acrylic, or 140-mil polycarbonate plastic. Such a template is called "rigid" in this patent specification. Preferably, a lower surface of the radial scanning template 112 makes a slippery contact with the skin surface in the presence of an ultrasound couplant such as gel between the template and the breast so that rotation is easily achieved even when the breast is under some degree (e.g., 4-12 lbs.) of downward compression. Despite the slippery contact with the breast, stabilization is provided by virtue of the generally circular shape of the radial scanning template 112. Preferably, a curled lip, e.g., as illustrated in FIG. 3b at 304a, is provided around the periphery 304 as well around the central hole 204 as illustrated at 204a, and a similar curled lip is provided at the edges of slot-shaped opening 202 as illustrated in FIG. 3c at 202a, to prevent skin cuts or chafing and provide additional comfort to the patient, similar to the way curled upper lips are provided on many paper, polystyrene, and PETE plastic drinking cups.

Figure 4A:
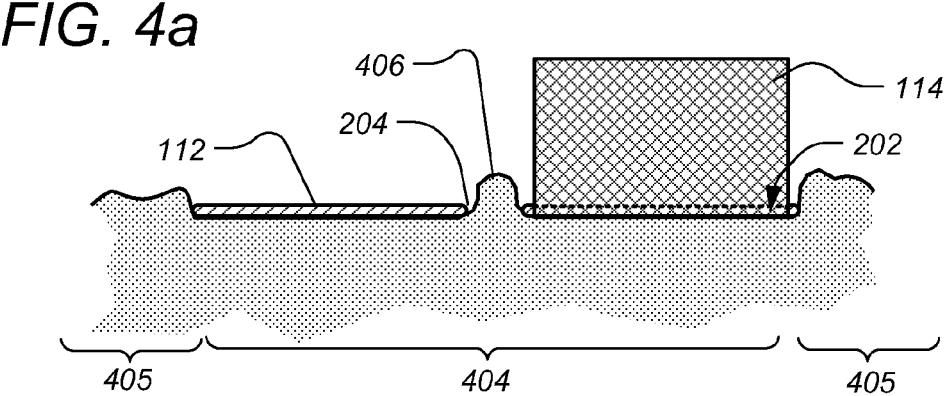
FIG. 4a is a cross-sectional view illustrating a patient's breast that is chestwardly compressed with an essentially planar template and is being scanned with an ultrasound transducer through a radially extending opening in the template.
Figure 4B:
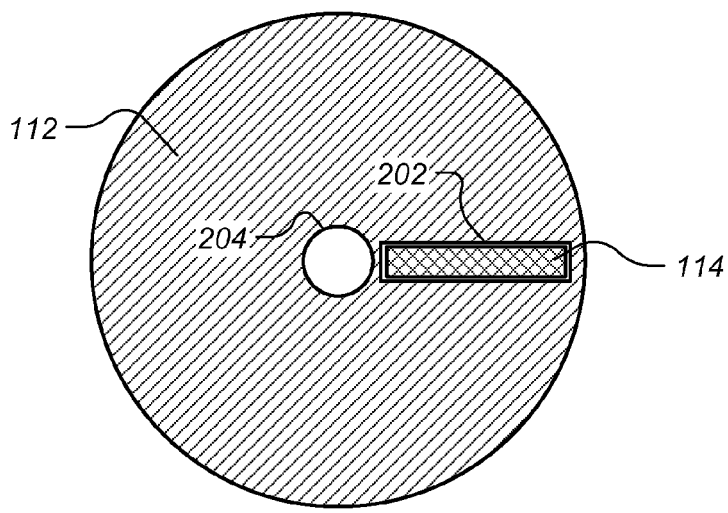
Figure 4C:
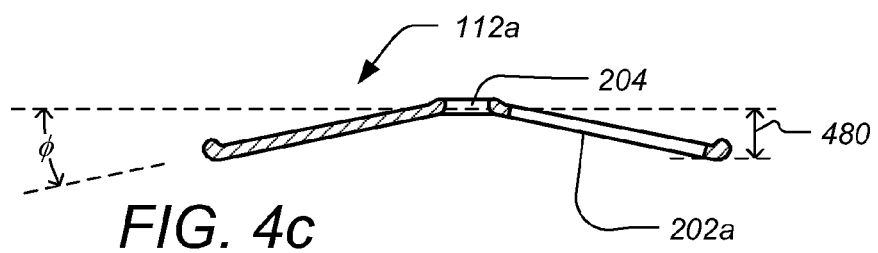
FIG. 4c is a cross-sectional view a scanning template that is otherwise similar to the template of FIGS. 4a and 4b but departs from absolute planarity by a departure angle φ that is greater than 2.5°.

FIG. 4a illustrates a side cut-away view of the essentially planar radial scanning template 112 as it chestwardly compresses a breast 404 having a nipple 406. The view can correspond to the axial or sagittal plane, and also illustrates patient tissue 405 that surrounds breast 404 laterally (e.g., in the coronal plane). The nipple 406 protrudes through the central opening 204. The transducer 114 scans the breast 404 through the slot-shaped opening 202. FIG. 4b illustrates a top conceptual view of FIG. 4a. FIG. 4c illustrates a template 112a that can be otherwise similar to the essentially planar template 112 but has a conical surface that departs from absolute planarity by a departure angle φ (phi) that is greater than 2.5°. Rather than shaped as a truncated cone, template 112a can be shaped as a shallow inverted bowl with a side curving in two orthogonal dimensions. A template with a departure angle φ greater than 2.5° can be used, if desired, in place of each of the essentially planar templates illustrated and discussed in this patent specification.

Whenever a departure angle is used that moves away from 0°, there is a penalty of scanning through increased breast thicknesses, which is measured as the distance from the scan surface to the chest wall. For example, if we define t (distance 480 in FIG. 4c) as the maximum differential thickness increase from the scan surface to the chest wall surface, then t could be expressed as the radial length of the transducer L times the sine of the departure angle φ:

$$t = L \sin \phi$$

The following table shows the relationship:

TABLE 1

| φ (degree) | Sin φ | L = 3 inch t (cm) | L = 4 inch t (cm) |
|---|---|---|---|
| 5 | 0.0872 | 0.7 | 0.9 |
| 10 | 0.1736 | 1.3 | 1.8 |
| 15 | 0.2588 | 2.0 | 2.6 |
| 20 | 0.3420 | 2.6 | 3.5 |
| 25 | 0.4226 | 3.2 | 4.3 |
| 30 | 0.5000 | 3.8 | 5.1 |

At 10 MHz, according to D'Astous and Foster, an increase in 2.5 cm in scan depth would increase attenuation by 25 to 50 dB, which would have a serious negative impact on image quality. Unless in extraordinary circumstances, either due to breast size or shape, where larger departure angles have to be used, for transducers having a radial length smaller than three inches, one should preferably consider using a departure angle of less than 30 degrees. For a three-inch transducer, one should preferably use a departure angle of less than 20 degrees. For a four-inch transducer, one should preferably use a departure angle of less than 15 degrees.

In the particular embodiment of FIGS. 4a and 4b, the slot-shaped opening 202 and the ultrasound transducer 114 both extend along substantially the entire distance from the central nipple hole 204 to the periphery of the radial scanning template such that a complete volumetric scan can be achieved in a single 360-degree rotation, with optional beam-steering for facilitating sub-areola imaging. If desired, the rotation angle can be extended by a few degrees to achieve some overlap of scanned breast tissue.

Figure 5:
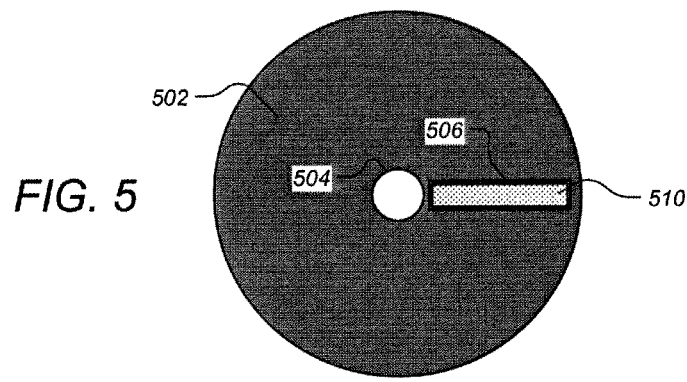
FIG. 5 is a plan view of a template with a membrane that is permeable to an ultrasound couplant such as a gel, through which an ultrasound transducer can scan the breast.

FIG. 5 illustrates a top view of a radial scanning template 502 according to a preferred embodiment, comprising a central opening 504, a slot-shaped opening 506, and a membrane 510 extending across the slot-like opening 506. The ultrasound transducer (not shown in this figure) scans the breast through the membrane 510. The membrane 510 preferably comprises a fabric material porous to ultrasound coupling agent such as gel, which can be advantageous in that air bubbles are reduced. As used in this patent specification, fabric refers generally to a material structure of interconnected or interleaved parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings. One particularly suitable material for the taut fabric sheet comprises a polyester organza material having a filament diameter of about 40 microns and a filament spacing of about 500 microns. However, the fabric membrane may comprise any of a variety of other fabrics that are substantially inelastic and generally porous to ultrasound couplants without departing from the scope of the present teachings. Examples include, but are not limited to, polyester chiffon fabrics and cloth fabrics comprising straight weaves of substantially inelastic fibers. If the weave is particularly tight, for example, as in cloth used in men's dress shirts or in many bed sheets, porosity can be achieved by additional treatment. The additional treatment can involve forming an array of perforations in the cloth or otherwise introducing irregularities that allow the ultrasound couplant to soak or seep through.

Figure 6:
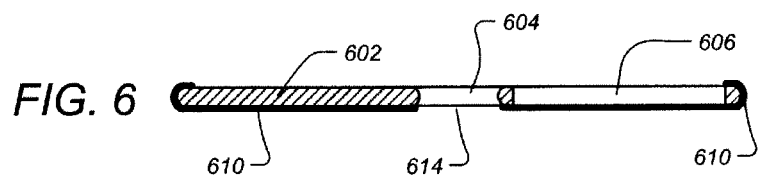
FIG. 6 is a cross-sectional view of the template of FIG. 5.

FIG. 6 illustrates a cross-sectional view of an essentially planar radial scanning template 602 according to a preferred embodiment, comprising a central opening 604, a slot-shaped opening 606, and a porous fabric membrane 610 in the form of a stretchable, generally circular fabric sock extending over the entire bottom-side of the planar template 602 (i.e., the side that faces and contacts the patient's breast) and across the slot-shaped opening 606 but preferably with a central hole 614 in the membrane for the nipple to protrude through. The sock can but need not extend over some or all of the upper side of template 602. According to another preferred embodiment, the porous fabric sock can be mounted on a circular or round frame that is snapped on or otherwise secured to the substantially planar radial scanning template 602. The ultrasound transducer (not shown in this figure) scans the breast through the porous fabric membrane 610 wetted with an acoustic coupler such as gel.

Figure 7:
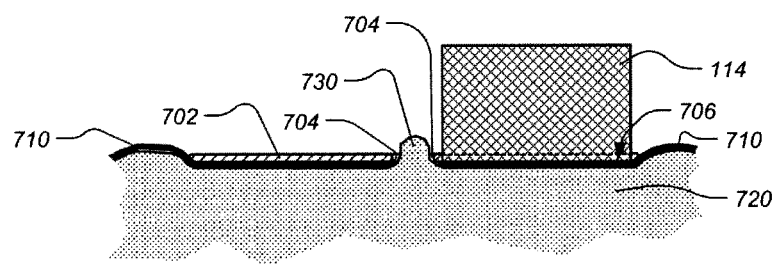
FIG. 7 is a cross-sectional view similar to FIG. 6 but additionally illustrating a portion of a breast being scanned and a scanning ultrasound transducer.

FIG. 7 illustrates a side view section of an essentially planar radial scanning template 702 according to a preferred embodiment, comprising a central opening 204, and a slot-shaped opening 706. The radial scanning template 702 is positioned over a patient (not shown except for a portion of the breast 720) wearing a brassiere-shaped article 710 comprising a porous membrane such as fabric at least over the breast and preferably with a central hole 714 for the nipple 730 to protrude through. The ultrasound transducer 114 scans the breast through the porous fabric article 710.

Figure 8:
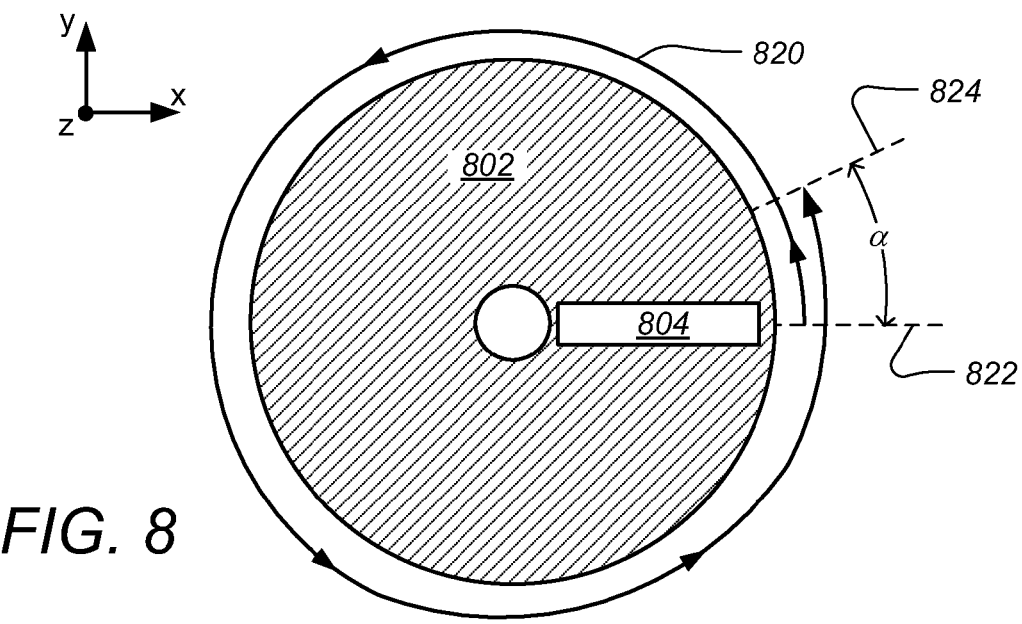
FIG. 8 is a top view of a template illustrating scan overlap angles.

FIG. 8 illustrates a top view of a radial scanning template 802 according to a preferred embodiment, comprising a single slot-shaped opening 804 corresponding to a single ultrasound transducer (not shown in this figure). The radial scanning template is preferably rotated 360° plus an overlap angle "α" (alpha) during the breast ultrasound scan, the overlap angle preferably being in a range, if desired, of 5° to 45°. See curved line 820. The coronal sector associated with the overlap angle alpha (i.e., the pie-shaped sector of the compressed breast subtending the arc between radial lines 822 and 824 in FIG. 8) is thus imaged twice. The dual volumetric images for the overlap sector can be advantageously used to reduce discontinuity artifacts in the volumetric representation of the breast that might otherwise occur along the radial line 822. In one preferred embodiment, the dual volumetric images are arithmetically averaged for smoothing over the discontinuity. However, more advanced stitching techniques can be used. Other mathematical methods for processing the dual volumetric images for reducing discontinuity artifacts exist and are within the scope of the preferred embodiments. One non-limiting example is weighted averaging in which the weights applied to one of the images of the overlap gradually decrease from unity to zero from the start to the end of the overlap zone while the weights applied to the other image in the overlap zone gradually increase from zero to unity. For example, the weights applied to the image obtained at the start of the circular scan increase with angular distance from line 822.

Figure 9:
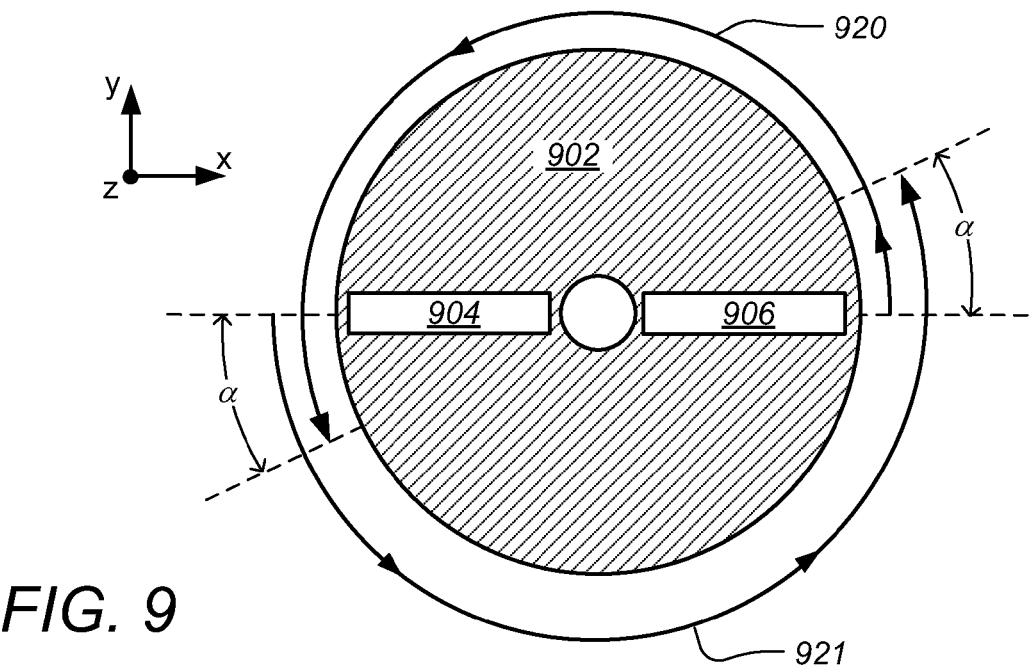
FIG. 9 is a top view of a template having two radial slots for two separate ultrasound transducers, according to some embodiments.

FIG. 9 illustrates a top view of a radial scanning template 902 according to a preferred embodiment, comprising two slot-shaped openings 904 and 906 corresponding to two ultrasound transducers (not shown) used during a scan. In one preferred embodiment, the radial scanning template 902 is preferably rotated by 180° plus, if desired, an overlap angle during the breast ultrasound scan, thereby reducing scanning time as compared to the use of a single ultrasound transducer. See curved lines 920-921. The image data from the two transducers is processed through stitching or other competing algorithms into a volumetric image of the breast.

In another preferred embodiment, the radial scanning template 902 is rotated through the full 360°, plus an overlap angle if desired, with the different ultrasound transducers being differently configured with respect to at least one imaging parameter. The resultant volumetric scans are then compounded or composited in any of a variety of advantageous ways, with or without different weighing, and/or can be viewed a separate images. Parameters that can be varied among the transducers include, but are not limited to, scan frequency, tilt angle, elevation beamwidth, scan mode (e.g., B-mode, harmonic, Doppler, elastography), in-plane acoustic interrogation angles, and different in-plane multi-angle compounding schemes. It should be apparent to a person of ordinary skill in the art after having read this patent specification to expand this scan configuration using 2 transducers to a scan configuration using a greater number of transducers.

Figure 10:
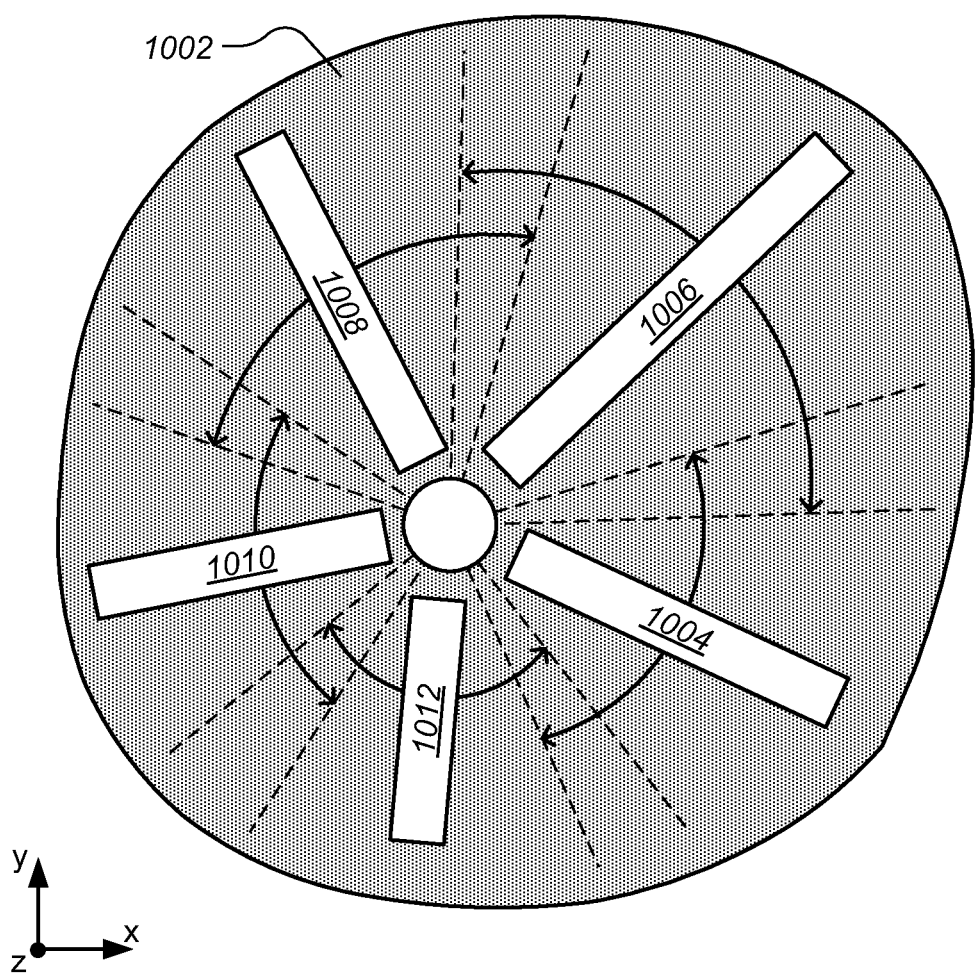
FIG. 10 is a top view of a template that has a non-circular outline and multiple radial slots through which respective transducers of different sizes and/or other characteristics scan respective sectors of a breast.

FIG. 10 illustrates a top view of a radial scanning template 1002 according to a preferred embodiment, comprising five slot-shaped openings 1004, 1006, 1008, 1010, and 1012 corresponding to five ultrasound transducers (not shown in this figure), each scanning the breast through a respective one of the openings directly or through a membrane (fabric) as described for an individual transducer in other embodiments. According to the preferred embodiment of FIG. 10, at least two of the ultrasound transducers have different radial lengths corresponding to different distances from the central nipple hole to the periphery of the radial scanning planar template. Each ultrasound transducer scans a different coronal sector of the breast. In the example of FIG. 10, which is for the left breast of a supine patient, the longest ultrasound transducer 1006 scans the coronal sector nearest the axilla, while the shortest ultrasound transducer 1012 scans an inferior medial sector of the breast. Accordingly, it can be appreciated that the general shape of a radial scan template according to the preferred embodiments is not limited to circular shapes with nipple openings at the geometric center, but rather includes different shapes and different locations of the nipple opening relative to the template's radial periphery. Likewise, a radial scan template according to the preferred embodiments is not limited to a circular shape, but rather can have a differently shaped periphery (e.g., oblong, elliptical, cam-shaped).

Figure 11A:
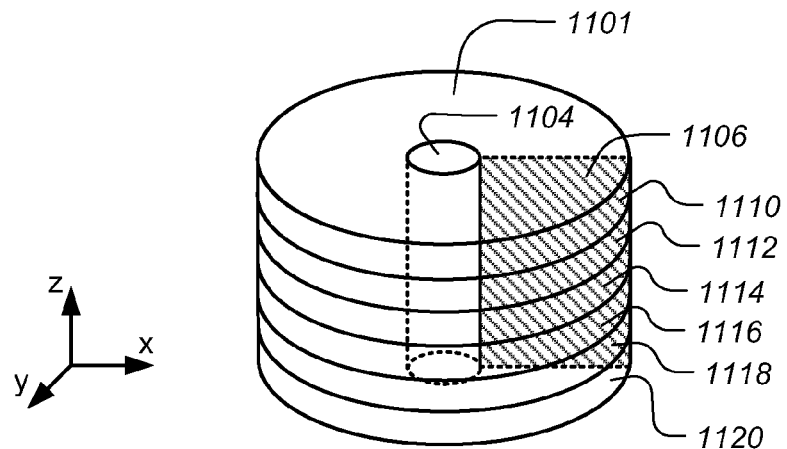
FIG. 11a illustrates a 3D scanned breast volume with coronal slices, according some embodiments.

The obtained ultrasound scans can be advantageously used in a variety of ways in accordance with the preferred embodiments. For example, it has been found that the acquired volumetric data is particularly advantageous for generating coronal slice images of the breast as shown in FIG. 11*a*, each preferably representing a slice that has a selected thickness in the z-direction (i.e., a direction toward or away from the patient's chest wall), although images of slices that have other orientations and may differ in thickness from each other also are with the scope of this patent specification. The slice thickness preferably is in the range of 0.5-2.0 mm, but can be in the range of 0.1-1.5 mm, or 0.1-2.0 mm, or 0.1-10.0 mm, and even a greater range. Another advantage of displaying coronal images is that they show lesion spiculations very well, which are an easily recognizable feature of a cancerous lesion.

Figure 11B:
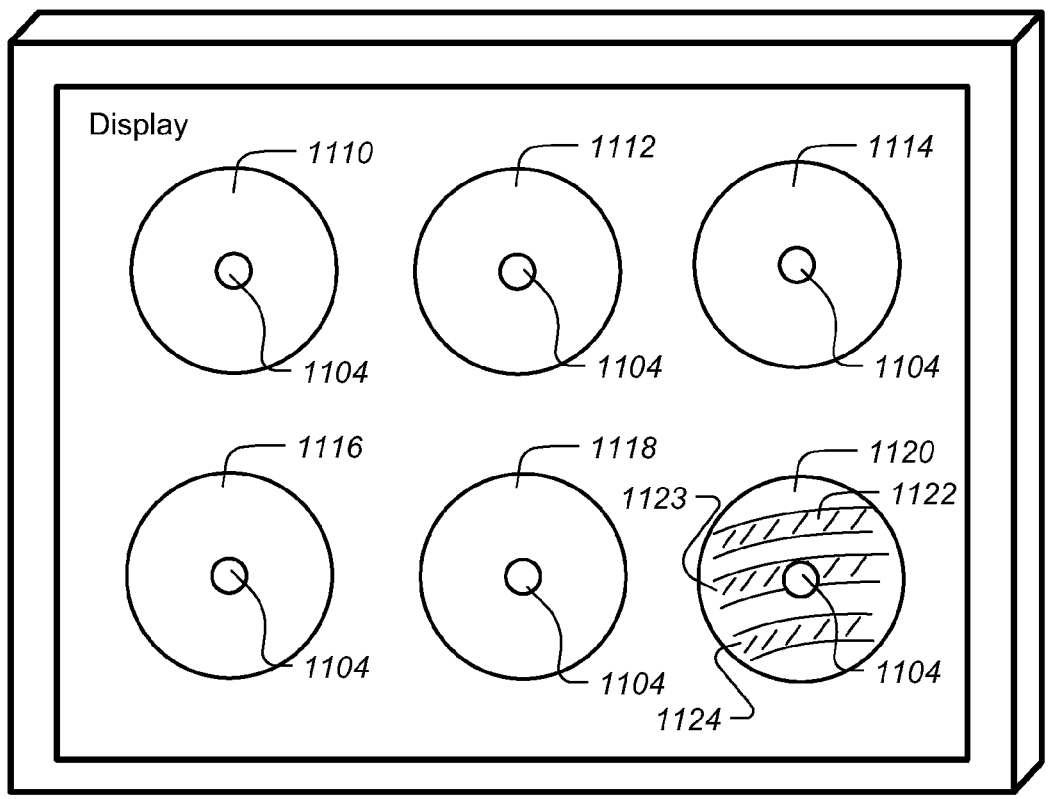
FIG. 11b illustrates a display of images of such coronal slices.

FIGS. 11*a* and 11*b* illustrate a 3D image 1101 of the breast represented as slices 1110-1120 reconstructed from 2D radial scan images such as image 1106, and the display of slice images 1110-1120 of slices of the 3D image. The 3D image 1101 is reconstructed from a great number of original 2D images from the radial scan that are transverse to the coronal plane. One such original 2D image 1106 is shown. Also shown is the central nipple hole 1104. The 3D image 1101 can be considered as divided into images of coronal slices of the breast (slices perpendicular to z-axis) 1110, 1112, 1114, 1116, 1118, 1120, etc., computed from the volumetric stack 1101 as known in the ultrasound imaging technology. FIG. 11*b* illustrates an example of how the slice images can be displayed to the physician or other health professional for interpretation. The last (bottom) slice 1120 is usually the slice at the chest wall or rib cage (which generally would show ribs 1122, 1123, 1124, etc. to confirm that adequate breast penetration has been achieved). The nipple and sub-areola regions, obtained either through beam-steering or manual scanning with a handheld transducer or otherwise can be displayed in stitched images or separately.

FIGS. 12*a* and 12*b* illustrate a single coronal slice image 1210 in a volumetric 3D image or stack 1201 of breast tissue, and a display of the slice image and of 2D images. Two original 2D radial scan images 1206 and 1208 bisect the 3D image, for example in a sagittal plane, and are spaced 180° from each other. The central nipple hole 1204 is also shown. FIG. 12*b* illustrates a display of 2D images 1206 and 1208 together with a display of 2D images 1236 and 1238, which are a pair orthogonal to the pair 1206 and 1208 (e.g., if the pair 1206-1208 are sagittal images than the pair 1236-1238 are axial images). Chest wall line 1209 is also shown. Notably, in this example the two orthogonal pairs of images are original 2D radial scan images, unlike similar pairs in known commercially available FFBUs, where orthogonal pairs are believed to be constructed from a volumetric reconstructed 3D image stack and consequently have reduced image quality. Typically, the reader would perform a quick review of coronal slices as shown in FIG. 11*b*, and/or perform a cine or other review of the coronal image in FIG. 12*b*, and/or a quick cine or other review of the original 2D images in FIG. 12*b*. A preferred way to perform a cine review of the original 2D images is simply to rotate the coronal slice 1210 to view the 180° pairs. Rotation of the coronal slice can be done with a control knob, by a cine review control, or by another interface, while other information such as the rotational angle, left or right breast, patient position, etc. are also displayed (not shown in FIG. 12*b*).

Figure 12C:
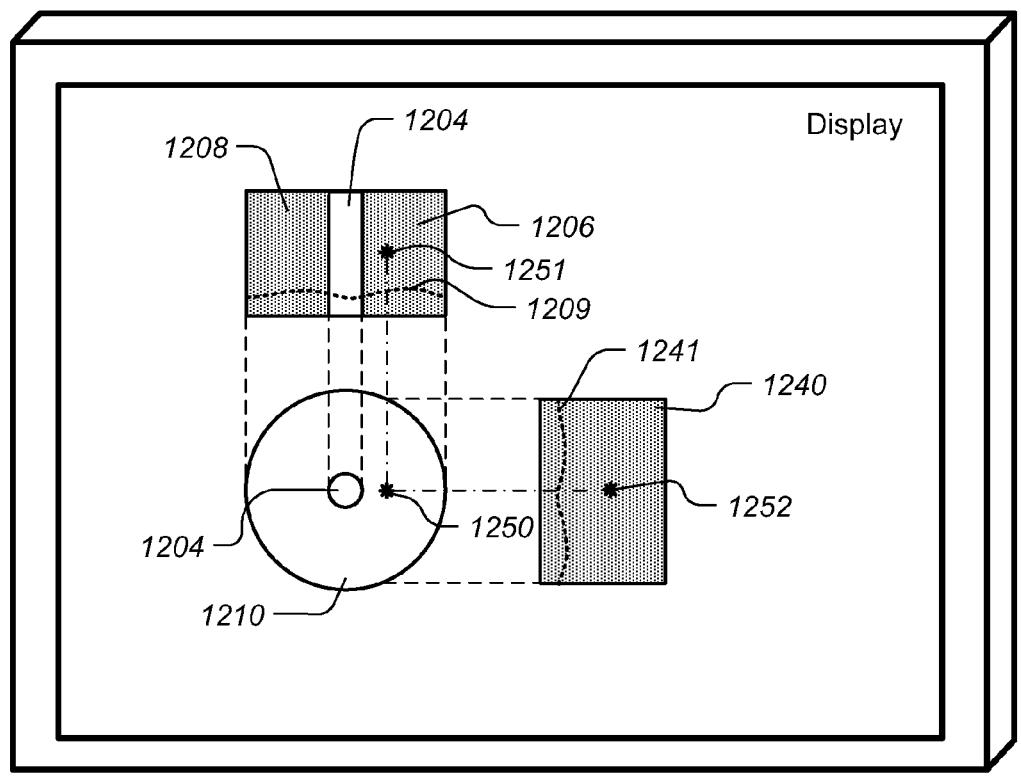
FIG. 12c illustrates a display of a coronal slice with an abnormality and of associated orthogonal views that contain the abnormality.

During the viewing of a coronal slice, an abnormality may be noted. As illustrated in FIG. 12*c*, when an abnormality 1250 in the coronal slice is found, with a click on the abnormality 1250 with a mouse or controller or by some other input, corresponding abnormality 1251 in the original 2D radial scan containing this abnormality can then be automatically pulled up and displayed through suitable algorithms programmed in frame 104 as known in ultrasound image processing technology. Similarly, a constructed orthogonal 2D image 1240 containing this abnormality 1252 can also be shown simultaneously. Also visible in constructed image 1240 is chestwall 1241.

Figure 13A:
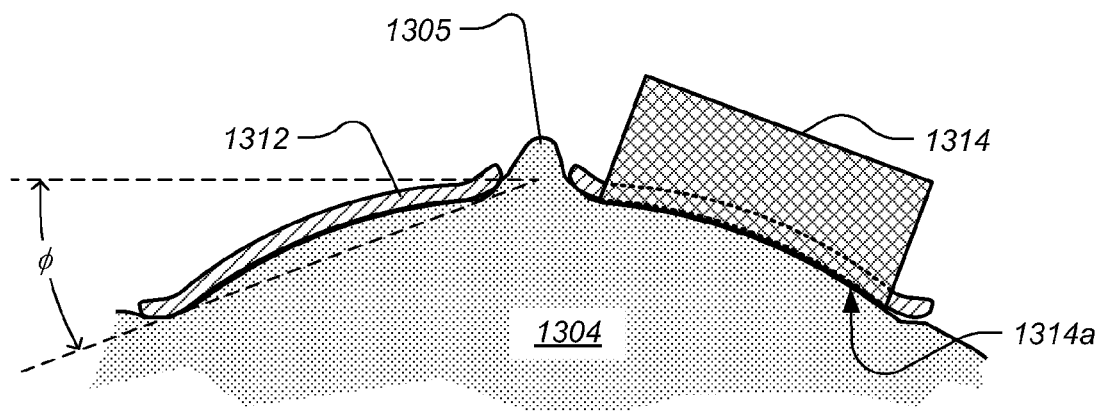
FIG. 13a illustrate a cross-section of breast being scanned with an ultrasound transducer that has a curved concave lower side and scans through an opening in a template that can be essentially planar or spherical or otherwise curved in two dimensions with a departure angle greater than 2.5°.
Figure 13B:
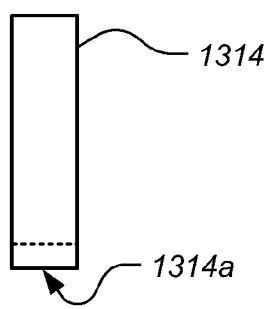
FIGS. 13b and 13c illustrate side views of ultrasound transducers according to some embodiments.
Figure 13C:
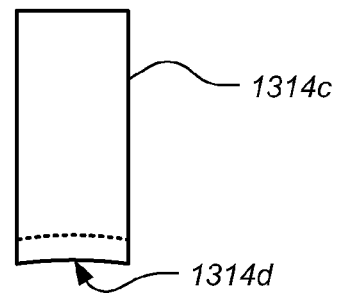

FIG. 13*a* illustrates the use of an ultrasound transducer 1314 that has a concavely curved bottom 1314*a* facing and scanning a patient's breast 1304 that is compressed with a rotating, concavely shaped template 1312 having a central opening through which the nipple 1305 protrudes. While template 1312 is illustrated as compoundly concavely curved, it can be planar or spherical in shape, and transducer 1314 can still have a similar concavely curved lower side 1314*a*, or it can have a generally planar lower side. In embodiments where several transducers concurrently scan a breast, e.g., as in FIG. 10, each transducer can have a concave lower side or some of the transducers (e.g., the shortest transducer(s)) can have straight lower sides, or all can have straight lower sides. In cases where the template 1312 is spherical such as shown in FIG. 13*a*, the departure angle φ can be greater than 2.5°, but preferably would not exceed about 20° as shown. FIG. 13*b* illustrates a side view of transducer 1314 having a curved lower side 1314*a* in a radial plane, but a straight lateral lower side. FIG. 13*c* illustrates a side view of a multi-array transducer 1314*c*, according to some embodiments. The multi-array transducer 1314*c* is wider as shown. Additionally, the lower curved side 1314*d* can be concavely curved both in the radial and in the lateral dimensions to match a concavely curved template 1312.

Figure 14:
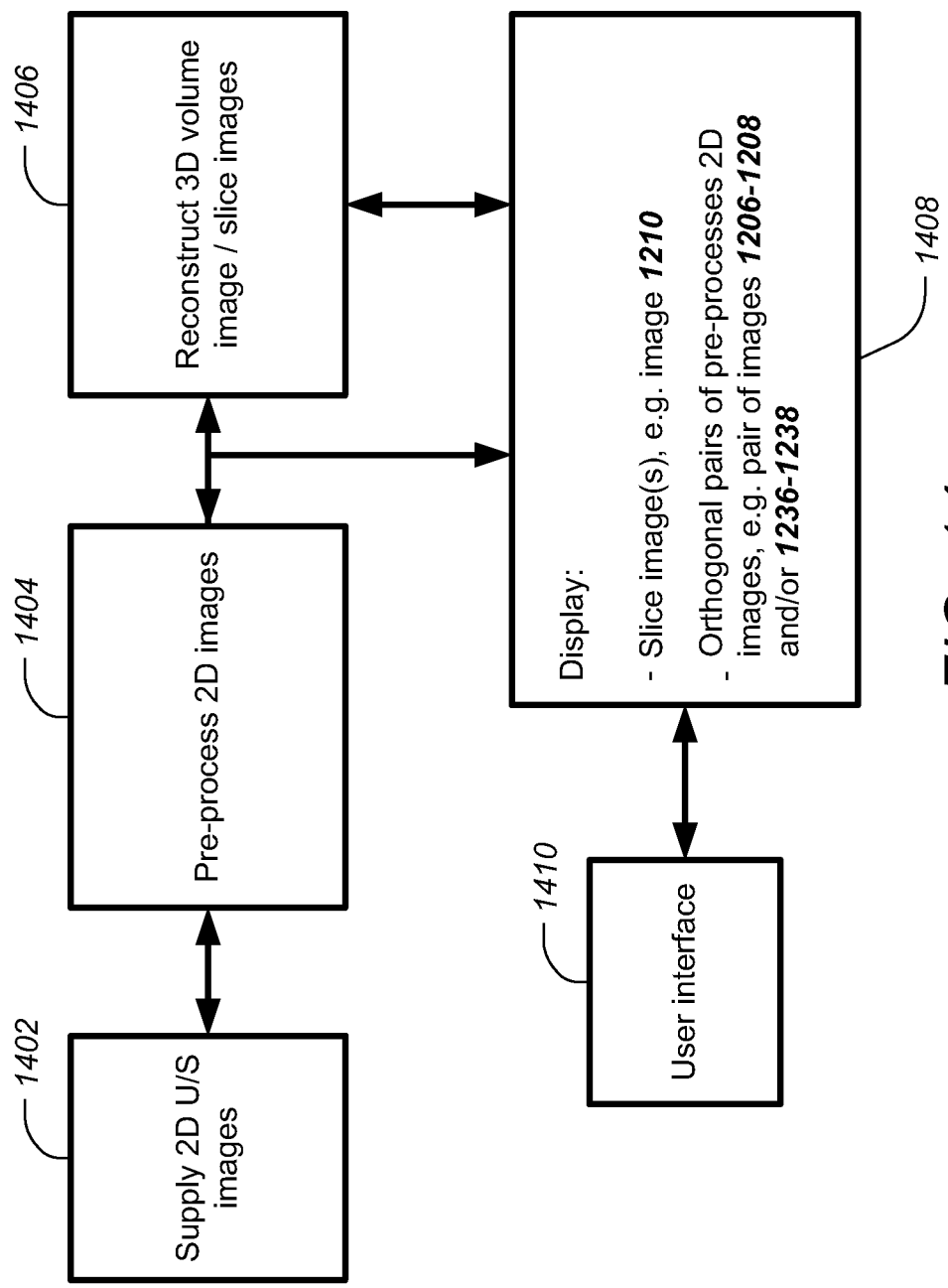
FIG. 14 illustrates in block diagram form a system for acquiring and processing ultrasound images and displaying resulting processed images in cooperation with a user interface.

FIG. 14 illustrates in block-diagram form certain computer-implemented facilities for carrying out scanning and image processing and display according to embodiments described above. One or more ultrasound transducers 1402 scanning the breast as described above supply raw 2D ultrasound images to a pre-processing facility 1404 that applies various algorithms to the raw images as known in the pertinent technology to generate pre-processed 2D images each representing a planar section of the breast conforming to a plane extending in the chestward direction (transverse to the coronal plane). These pre-processed 2D images are supplied to a facility 1406 that reconstructs from them a 3D image of the breast and, if the 3D image is in a form different from a stack of coronal slice images representing breast slices of selected thicknesses (e.g., as a non-limiting example, slices that are 0.5-10 mm thick) the facility generates such slice images from the 3D image of the breast. Thus far, the operation is similar to the known generation of 2D and 3D images and slice images in commercially available FFBU devices, except that the raw 2D images are generated using the essentially planar template described above. A display facility 1408 receives the pre-processed 2D images from facility 1404 and the 3D image and/or the coronal slice images from reconstruction facility 1406. The display facility 1408 includes one or more computer display screens and computerized processing circuits and software, and operates under the control of a user interface 1410 to generate and display slice images such as 1110 through 1120 as illustrated in FIGS. 11*a* and 11*b* and/or a slice image such as 1210 together with pairs of pre-processed 2D images such as 1206-1208 and 1236-1238 illustrated in FIGS. 12*a* and 12*b*. The coronal slice images of FIG. 11*b* can be displayed concurrently or in sequence or in a cine mode. Per operator control through interface 1410, the images can be moved on the display screen or superimposed or one or more can be changed, such as by changing the orientation of the slice that the image represents, or the thickness of the slice, or the transparency of one or more superimposed images, or the type of projection that generated the slice (e.g., minimum or maximum intensity projection) by applying image processing techniques known in the ultrasound imaging field and/or in other image processing and display fields such as postproduction of still or video images. Similarly, the images illustrated in FIG. 12*b* can be displayed in the illustrated format or in other formats known in the pertinent technology. As non-limiting examples, the slice image 1210 of FIG. 12*b* can be changed to represent a slice that has a different orientation or thickness or to an image of the slice that was generated in a different way (e.g., by a different type of projection), and the 2D images or FIG. 12*b* also can be varied under control of inputs from interface 1410, such as by rotating their planes around an axis normal to or only transverse to the coronal plane, by changing the angle between the planes of the two pairs of the 2D images, by changing the range of pixel values in the images (i.e., by controlling the window width of the images), and in other ways known in the technology of displaying pixel value images. Some or all of the facilities illustrated in FIG. 14 can be implemented by programming the computing equipment in frame 104 or FIG. 1, or by carrying out processing in a separate computer equipment connected thereto, or in a workstation that is remote from frame 104 but is coupled therewith to receive the 2D images that the transducer(s) generate. The software controlling the operation of the equipment illustrated in FIGS. 1 and 14 can be stored in non-transitory form in computer-readable media to form a program product.

According to some embodiments, images from prior examinations could also be shown together with the images of the current examination of a patient using display facility 1408 to view changes over time. According to some embodiments, an image that represents the difference over time between the images is displayed using display facility 1408. According to yet other embodiments, CAD (computer aided detection and diagnosis) results and/or other image enhancing results can also be displayed using display facility 1408.

Whereas many alterations and modifications of the examples described above will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, compress, rotate, and otherwise manipulate the scanning template, whether the scanning template is permanently used and re-used for different patients or is disposable for each patient, without departing from the scope of the present teachings. Moreover, in one or more alternative preferred embodiments, the basic profile of the radial scanning template can be elliptically shaped, etc., rather than strictly circular-shaped as indicated in some of the attached drawings. The scanning surface of the ultrasound transducer can be arched or make to conform to another curved surface in a similar manner, if desired. Therefore, references to the details of the embodiments are not intended to limit their scope.

What is claimed is:

1. An apparatus for ultrasonically scanning a breast, comprising:
    an essentially planar radial scanning template configured to contact and compress and flatten the breast chestwardly while the breast is facing up, wherein the template has a rounded periphery and a nipple hole configured for a breast nipple to protrude upwardly therethrough, and the template has one or more elongated, slot-shaped openings extending from the nipple hole toward a periphery of the template;
    one or more elongated ultrasound transducers each aligned with a respective one of the one or more slot-shaped openings;
    said template being configured to rotate over the breast while compressing the breast, and said one or more transducers being configured to rotate with the template to scan the breast ultrasonically through the respective one or more slot-shaped openings and to generate 2D ultrasound images of the breast;

an actuator configured to automatically rotate the template for said scanning; and a computer-implemented image processing and display facility associated with the one or more transducers and configured to receive and process the 2D images into images of slices of the breast that have selected thicknesses and orientations, and further configured to display, under operator control, at least one or more images selected from the slice images.

2. The apparatus of claim 1 in which the image processing and display facility is configured to display one or more images selected from the 2D images concurrently with the display of one or more images selected from the slice images.

3. The apparatus of claim 1 in which the image processing and display facility is configured to concurrently display a first 2D image and a second 2D image, both of which are selected from the 2D images such that the first and second 2D images are 180 degrees apart.

4. The apparatus of claim 1 in which the template includes two or more slot-shaped openings and two or more ultrasound transducers each aligned with a respective one of the openings.

5. The apparatus of claim 4 in which two or more of the ultrasound transducers differ from each other in radial length.

6. The apparatus of claim 4 in which two or more of the ultrasound transducers differ from each other in characteristics in addition to any differences in radial length.

7. The apparatus of claim 4 in which the template has a non-circular shape and is configured to have greater radial dimension in a sector configured to approach an axilla of a patient when the patient's breast is being scanned with the transducers.

8. The apparatus of claim 1 in which edges of the template are provided with rounded edges comprising upturned lips at least at a radial periphery of the template.

9. The apparatus of claim 8 in which said rounded edges include edges at the one or more openings in the template.

10. The apparatus of claim 1 in which at least one of the one or more transducers has an underside configured to contact the breast with a concave surface.

11. The apparatus of claim 1 in which the template is configured to scan the breast with one or more transducers over a scan angle that exceeds 360° by an overlap angle.

12. The apparatus of claim 11 in which the template is configured to scan through an overlap angle that is in the range of 5°-45°.

13. The apparatus of claim 1 including a membrane permeable to an acoustic couplant that extends across one or more of the slot-shaped openings, and wherein one or more of the ultrasound transducers scan the breast through the membrane.

14. A method for ultrasonically scanning a breast, comprising:

contacting and compressing and flattening the breast chestwardly with an essentially planar radial scanning template while the breast is facing up, wherein the template has a rounded periphery and a nipple hole configured for a breast nipple to protrude upwardly therethrough, and the template has one or more elongated, slot-shaped openings extending from the nipple hole toward a periphery of the template;

rotating said template over the breast while compressing the breast and while scanning the breast with one or more elongated ultrasound transducers each aligned with a respective one of the one or more slot-shaped openings to thereby generate 2D ultrasound images of the breast; and computer-processing the 2D images into images of images of slices of the breast that have selected thicknesses and orientations; and displaying, under operator control, at least one or more images selected from the slice images.

15. The method of claim 14 in which the image processing and display steps are configured to display one or more images selected from the 2D images concurrently with the display of one or more images selected from the slice images.

16. The method of claim 14 in which the image processing and display steps are configured to concurrently display a first 2D image and a second 2D image, both of which are selected from the 2D images such that the first and second 2D images are 180 degrees apart.

17. The method of claim 14 in which the scanning includes scanning the breast with two or more ultrasound transducers each aligned with a respective one of the slot-shaped openings.

18. The method of claim 17 in which the scanning includes scanning the breast with two or more ultrasound transducers that differ from each other in radial length.

19. The method of claim 17 in which the scanning includes scanning the breast with two or more ultrasound transducers that differ from each other in characteristics in addition to any differences in radial length.

20. The method of claim 17 in which the scanning includes using a template that has a non-circular shape and is configured to have greater radial dimension in a sector configured to approach an axilla of a patient when the patient's breast is being scanned with the transducers.

21. The method of claim 14 in which the scanning includes using a template with rounded edges comprising upturned lips lips at least at a radial periphery of the template.

22. The method of claim 14 in which the scanning includes using a template with rounded edges at one or more of the openings in the template.

23. The method of claim 14 in which the scanning includes scanning the breast with at least one transducer that has an underside configured to contact the breast with a concave surface.

24. The method of claim 14 in which the scanning includes scanning the breast with one or more transducers over a scan angle that exceeds 360° by an overlap angle.

25. The method of claim 24 in which the overlap angle that is in the range of 5°-45°.

26. The method of claim 14 in which the scanning includes scanning the breast with at least one ultrasound transducer through a membrane attached to the template and permeable to an acoustic couplant that extends across at least one of the one of more slot-shaped openings.

* * * * *